United States Patent
Prakash et al.

(10) Patent No.: US 9,880,098 B2
(45) Date of Patent: Jan. 30, 2018

(54) METHOD AND SYSTEMS FOR QUANTIFYING DIFFERENCES BETWEEN COLORED SURFACES

(71) Applicant: AXALTA COATING SYSTEMS IP CO., LLC, Wilmington, DE (US)

(72) Inventors: Arun Prakash, West Chester, PA (US); Mahnaz Mohammadi, Moorestown, NJ (US)

(73) Assignee: AXALTA COATINGS SYSTEMS IP CO., LLC, Wilmington, DE (US)

( * ) Notice: Subject to any disclaimer, the term of this patent is extended or adjusted under 35 U.S.C. 154(b) by 116 days.

(21) Appl. No.: 14/885,517

(22) Filed: Oct. 16, 2015

(65) Prior Publication Data
US 2016/0116398 A1   Apr. 28, 2016

Related U.S. Application Data

(60) Provisional application No. 62/069,406, filed on Oct. 28, 2014.

(51) Int. Cl.
| | |
|---|---|
| G01J 3/46 | (2006.01) |
| G01N 21/57 | (2006.01) |
| G01J 3/02 | (2006.01) |
| G01J 3/52 | (2006.01) |
| G01J 3/50 | (2006.01) |

(52) U.S. Cl.
CPC .............. *G01N 21/57* (2013.01); *G01J 3/02* (2013.01); *G01J 3/46* (2013.01); *G01J 3/50* (2013.01); *G01J 3/52* (2013.01); *G01N 2021/575* (2013.01)

(58) Field of Classification Search
CPC ........ G01J 3/02; G01J 3/46; G01J 3/52; G01J 3/51; G01J 3/50; G01N 21/25
See application file for complete search history.

(56) References Cited

U.S. PATENT DOCUMENTS

| | | | |
|---|---|---|---|
| 2013/0209790 A1* | 8/2013 | Geissler | B82Y 30/00 428/329 |
| 2015/0192516 A1* | 7/2015 | Choulet | G01N 21/86 356/445 |

OTHER PUBLICATIONS

Kigle-Bockler, G. "New BYK-mac, Total color Impression of Effect Coatings", BYK-mac Presentation, BYK Additives & Instruments, 2008, pp. 1-44.

* cited by examiner

*Primary Examiner* — Abdullahi Nur
(74) *Attorney, Agent, or Firm* — Lorenz & Kopf LLP

(57) ABSTRACT

A system and method of quantifying a difference between gonioapparent colored surfaces includes determining a lightness ($L^*$), a sparkle area (Sa), and a sparkle intensity (Si) of the first and second surfaces at a first aspecular angle and at a second aspecular angle. A sparkle metric (SpkM) to quantify the difference between the first and second surfaces is calculated utilizing the lightness ($L^*$), the sparkle area (Sa), and the sparkle intensity (Si) of the first and second surfaces at the first and second aspecular angles.

21 Claims, 4 Drawing Sheets

METHOD AND SYSTEMS FOR QUANTIFYING DIFFERENCES BETWEEN COLORED SURFACES

CROSS-REFERENCE TO RELATED APPLICATIONS

This application claims the benefit of U.S. Provisional Application No. 62/069,406 filed Oct. 28, 2014.

TECHNICAL FIELD

The technical field relates generally to methods and systems for comparing colored surfaces and more particularly relates to methods and systems for comparing colored surfaces which include gonioapparent pigments.

BACKGROUND

Many colored surfaces, e.g., exterior paneling of automobiles, include gonioapparent pigments which impact the surface's color and appearance. These pigments may include, but are certainly not limited to, flakes formed from metals, silica, pearlescent pigments, and/or interference pigments. As a result of these pigments, gonioapparent colored surfaces have colors and spatial appearances that vary as with changes in the amount of illumination (i.e., the amount of light on the surface), viewing geometries (i.e., the angle of viewing the surface), and/or illumination geometries. An important aspect of spatial appearance is "sparkle" and how it changes with changing illumination and viewing geometries.

When attempting to match a pair of colored surfaces, for example, when attempting to find a matching paint formula to repaint a portion of an automobile, the presence of gonioapparent pigments adds a high degree of complexity to the process. Attempts to match gonioapprent colored surfaces often require human inspection, which can be quite subjective and often prone to error.

As such, it is desirable to present a method and system which provides a reliable process for matching gionioapparent colored surfaces, with higher precision than is found with human inspection. In addition, other desirable features and characteristics will become apparent from the subsequent summary and detailed description, and the appended claims, taken in conjunction with the accompanying drawings and this background.

SUMMARY

In one exemplary embodiment, a method of quantifying a difference between a first gonioapparent surface and a second gonioapparent surface includes determining a first set of correlated lightness (L*), sparkle area ($S_a$), and sparkle intensity ($S_i$) of the first gonioapparent surface and the second gonioapparent surface at a first aspecular angle. The method also includes generating a first set of sparkle grade ($S_g$) of the first surface and the second surface based on the respective first set of sparkle area ($S_a$) and sparkle intensity ($S_i$) of the first gonioapparent surface and the second gonioapparent surface. The method further includes calculating a first set of normalized sparkle grade difference tolerances ($K_{sg}$) with a processor utilizing the first set of lightness (L*), sparkle grade ($S_g$), and a predefined first visual tolerance function ($K_{sg}$) based on model lightness (L*) and model sparkle grade ($S_g$) derived from model sparkle intensity ($S_i$) and model sparkle area ($S_i$) obtained from a plurality of model surfaces at a plurality of aspecular angles. A sparkle metric (SpkM) is calculated with a processor to produce a quantified difference between the first and second gonioapparent surfaces according to the first set of lightness (L*), the first set of sparkle grade ($S_g$), and the first set of normalized sparkle grade difference tolerances ($K_{sg}$).

In one exemplary embodiment, a system for quantifying a difference between a first gonioapparent colored surface and a second gonioapparent colored surface includes a measurement device. The measurement device includes a light source for illuminating the first surface at a first aspecular angle and at a second aspecular angle different from the first angle and the second surface at the first aspecular angle and at the second aspecular angle. The measurement device also includes a sensor for sensing light reflected off the first and second surfaces at the respective first and second aspecular angles. The measurement device further includes a processor in communication with the sensor for determining a lightness (L*), a sparkle area (Sa), and a sparkle intensity (Si) of the first and second surfaces at the respective first and second aspecular angles. The system also includes a computer configured to receive the lightness (L*), a sparkle area (Sa), and a sparkle intensity (Si) of the first and second surfaces at the first and second aspecular angles. The computer is also configured to calculate a sparkle metric (SpkM) to quantify the difference between the first and second surfaces utilizing the lightness (L*), the sparkle area (Sa), and the sparkle intensity (Si) of the first and second surfaces at the first and second aspecular angles.

BRIEF DESCRIPTION OF THE DRAWINGS

Other advantages of the disclosed subject matter will be readily appreciated, as the same becomes better understood by reference to the following detailed description when considered in connection with the accompanying drawings wherein.

DETAILED DESCRIPTION

Figure 1:
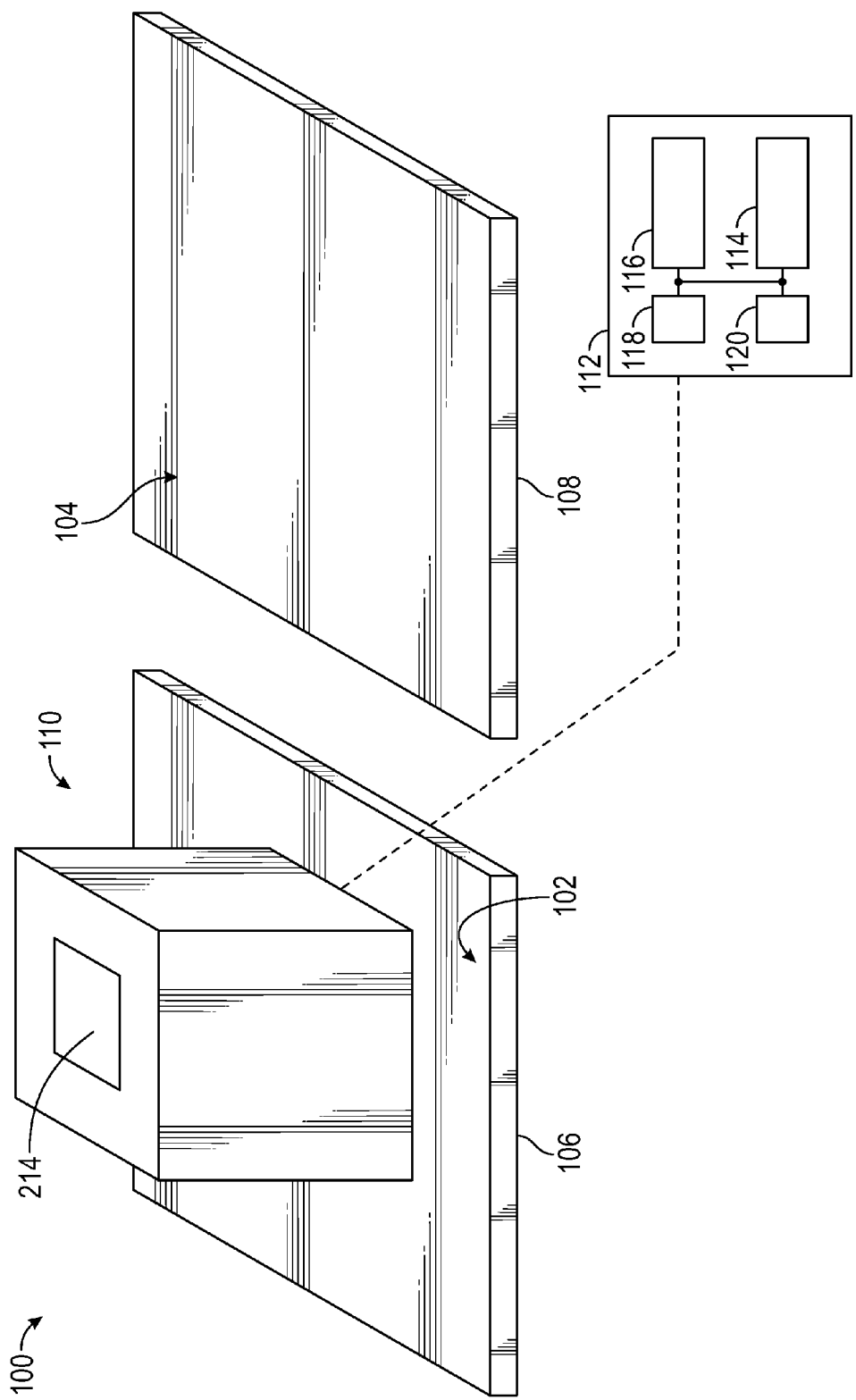
FIG. 1 is a perspective view of a first surface and a second surface with a measurement device disposed on the first surface according to one embodiment.

Referring to the Figures, wherein like numerals indicate like parts throughout the several views, a system 100 and method 400 for quantifying differences between gonioapparent colored surfaces 102, 104 is shown and described herein. The system 100 may be utilized to implement the method 400. However, it should be appreciated that the method 400 may be implemented utilizing various other devices and components than those specifically recited hereafter.

In the exemplary embodiments, the gonioapparent colored surfaces 102, 104 are surfaces including a gonioapparent flake (not shown). Those skilled in the art appreciate numerous types of gonioapparent flake that may be mixed with paint or other coatings, including, but certainly not limited to, metals (e.g., aluminum) and silicas (e.g., mica). The system 100 and method 400 described herein may be utilized to quantify differences between any number of colored surfaces 102, 104. However, for purposes of simplicity and clarity in description, typically only a first surface 102 and a second surface 104 shall be described hereafter.

In the exemplary embodiments, the first gonioapparent colored surface 102 (the "first surface") is a "standard", i.e., the first surface 102 is a sample which other samples are compared to. Conversely, the second gonioapparent colored surface 104 (the "second surface") may be referred to as a "batch", i.e., an attempt to match the standard. For example, the first surface 102 may reflect an original formula of paint that was created when the particular formula was created, while the second surface 104 reflects a coating that is an attempt to match the original formula. The second surface 104 may be included, for example, on an exterior paneling of an automobile. In particular, the exterior paneling may include a gonioapparent surface coating as the second surface 104, with the gonioapparent surface coating having at least one gonioapparent flake. However, it should be appreciated that the system 100 and method 400 described herein may be implemented with any two surfaces 102, 104, whether or not one is denoted a "standard".

Referring to FIG. 1, the system 100 includes a measurement device 110 configured to measure various characteristics of the surfaces 102, 104. In the exemplary embodiment shown in FIG. 1, the measurement device 110 is shown disposed atop the first surface 102. However, it should be appreciated that the measurement device 110 of the exemplary embodiment is portable, such that it may be moved to the second surface 104 or any other surface (not shown). In other embodiments (not shown), the measurement device 110 may be fixed at a location. In yet other embodiments (not shown), the measurement device 110 may be attached to a robotic arm to be moved automatically. In further embodiments (not shown), the measurement device 110 may be configured to measure characteristics of multiple surfaces 102, 104 simultaneously.

Figure 2:
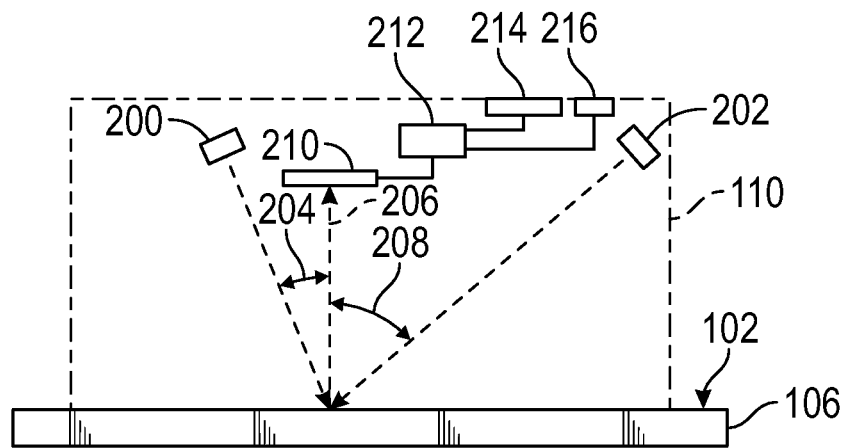
FIG. 2 is block diagram of the measurement device showing a plurality of light sources illuminating the first surface at a plurality of angles according to one embodiment.

Referring now to FIG. 2, the measurement device 110 includes at least one light source 200, 202 for illuminating the surface 102 that is being measured. In the embodiment shown in FIG. 2, the measurement device 110 is shown disposed on the first surface 102. However, it is to be appreciated that the measurement device 110 may be moved to the second surface 104 and/or any other surface (not shown). Also, as stated above, the measurement device 110 may be configured to illuminate multiple surfaces 102, 104 simultaneously.

In the exemplary embodiment shown in FIG. 2, the measurement device 110 includes a first light source 200 and a second light source 202. In the exemplary embodiment, the first light source 200 illuminates the first surface 102 at a first aspecular angle 204 with respect to a line 206 normal to the first surface 102. The second light source 202 illuminates the first surface 102 at a second aspecular angle 208 with respect to the line 206. The second aspecular angle 208 is different from the first aspecular angle 204. Specifically, in the embodiment shown in FIG. 2, the first aspecular angle 204 is about 15° and the second aspecular angle 208 is about 45°.

Figure 3:
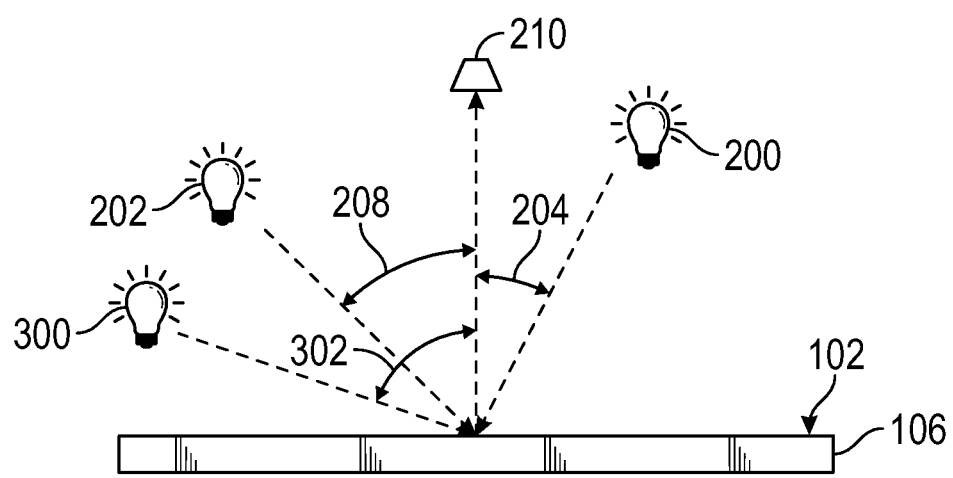
FIG. 3 is block diagram showing a plurality of light sources illuminating the first surface at a plurality of angles according to another embodiment.

In other embodiments, more than two light sources 200, 202 may be utilized. Furthermore, more than two aspecular angles may be utilized. For instance, with reference to FIG. 3, a third light source 300 is utilized in addition to the first and second light sources 200, 202. Accordingly, in addition to the first aspecular angle 204 of about 15° and the second aspecular angle 208 of about 45°, a third aspecular angle 302 of about 75° is utilized.

When referencing the aspecular angles 204, 208, 302 the term "about" refers to a ±5° margin of error. In other embodiments (not shown), the aspecular angles 204, 208, 302 may be different from the aspecular angles 204, 208, 302 shown in FIGS. 2 and 3 and described herein. As such, the terms "first aspecular angle", "second aspecular angle", and "third aspecular angle" should not be read as limiting the disclosure to the use of only two or three aspecular angles.

The measurement device 110 also includes a sensor 210 for sensing light reflected off the first surface 102. In the exemplary embodiment shown in FIG. 2, the sensor 210 is disposed at the line 206 normal to the surface 104. The sensor 210 may be a charge-coupled device ("CCD") or other suitable apparatus for detection of light. Of course, multiple sensors 210 may alternatively be utilized.

The measurement device 110 also includes a processor 212 in communication with the sensor 210. The processor 212 is configured to perform calculations and/or execute instructions, i.e., run a computer program. The processor 212 can be any custom made or commercially available processor, a central processing unit ("CPU"), a semiconductor based microprocessor (in the form of a microchip or chip set), an application specific integrated circuit ("ASIC"), or generally any device for executing instructions and/or performing calculations.

In the exemplary embodiment, the processor 212 of the measurement device 110 is configured to determine lightness $L^*$, a sparkle area $S_a$, and a sparkle intensity $S_i$ of the surfaces 102, 104 at the first aspecular angle 204 and at the second aspecular angle 208. More specifically, in the exemplary embodiment, the processor 212 is configured to determine a first set of correlated lightness $L^*$, sparkle area $S_a$, and sparkle intensity $S_i$ of the first gonioapparent surface 102 and the second gonioapparent surface 104 at the first aspecular angle 204 and a second set of correlated lightness $L^*$, sparkle area $S_a$, and sparkle intensity $S_i$ of the first gonioapparent surface 102 and the second gonioapparent surface 104 at the second aspecular angle 208. The term "correlated" refers to measurements from the same surface 102, 104, or the same or adjacent location representing the surface 102, 104, at a specific aspecular angle 204, 208.

Lightness $L^*$, for solid colors, is defined as a number between 0 and 100 wherein 0 represents black and 100 represents white. However, in gonioapparent surfaces, lightness $L^*$ can range from 0 to about 140. The term lightness $L^*$, as used in the exemplary embodiment, refers to the dimension L as defined in the CIELab color space, as is appreciated by those skilled in the art. The sparkle area $S_a$ refers to the area occupied by the gonioapparent flake as measured by the sensor 210. In one embodiment, the sparkle area $S_a$ is the area of an illuminated portion of a surface with spots that are strikingly brighter than their immediate surroundings. The sparkle intensity $S_i$ refers to the intensity of light reflected off the gonioapparent flake as measured by the sensor 210. In one embodiment, the sparkle intensity $S_i$ is the contrast between the appearance highlights on the particles of a gonioapparent pigment and their immediate surroundings.

The processor 212 may also be configured to calculate a sparkle grade $S_g$. The sparkle grade $S_g$ may be computed utilizing the sparkle area $S_a$ and the sparkle intensity $S_i$.

The measurement device 110 of the exemplary embodiment also includes a display 214 in communication with the processor 212. The display 214 is configured to display values and/or other data that are measured and/or calculated by the measurement device 110. For instance, in one embodiment, the display 214 may display the lightness L*, sparkle area $S_a$, sparkle intensity $S_i$, and sparkle grade $S_g$.

The measurement device 110 may also include a data transfer apparatus 216. The data transfer apparatus 216 may implemented with a port to transfer data via a cable, e.g., a USB cable. Alternatively, the data transfer apparatus 216 may be implemented with a radio for transferring data wirelessly. Other implementations of the data transfer apparatus 216 will be apparent to those skilled in the art.

In the exemplary embodiment, the measurement device 110 may be implemented with a BYK-mac spectrophotometer as manufactured by BYK-Gardner USA, located in Columbia, Md., a subsidiary of ALTANA AG of Wesel, Germany. However, it should be appreciated that other products may be suitable for implementing the measurement device 110 as described herein.

Referring again to FIG. 1, the system 100 further includes a computer 112. The computer 112 of the embodiment shown in FIG. 1 includes an input device 114, an output device 116, a processor 118, and a memory 120. As can be appreciated, the computer 112 can include any computing device, including but not limited to, a desktop computer, a laptop, a server, a portable handheld device, or any other electronic device that includes a memory 120 and a processor 118. The input device 114 may include, but is not limited to, a keyboard, a mouse, a serial port (e.g., a USB port), a network port, and a microphone. The output device 116 may include, but is not limited to, a display, a speaker, the serial port, and the network port.

In various embodiments, the memory 120 stores instructions that can be performed by the processor 118 and/or other data. The instructions stored in memory 120 may include one or more separate programs, each of which comprises an ordered listing of executable instructions for implementing logical functions. When the computer 112 is in operation, the processor 118 is configured to execute the instructions stored within the memory 120, to communicate data to and from the memory 120, and to generally control operations of the computer 112 pursuant to the instructions. The processor 118 can be any custom made or commercially available processor, a central processing unit (CPU), an auxiliary processor among several processors associated with the computer 112, a semiconductor based microprocessor (in the form of a microchip or chip set), a macroprocessor, or generally any device for executing instructions.

The computer 112 is configured to receive a first set of correlated lightness L*, sparkle area $S_a$, and sparkle intensity $S_i$ of the first sample 102 and the second sample 104 at the first aspecular angle 204. The computer 112 may also receive the sparkle grade $S_g$ of the first and second samples 102, 104 at the first aspecular angle 204. In one exemplary embodiment, the computer 112 is configured to also receive a second set of correlated lightness L*, sparkle area $S_a$, and sparkle intensity $S_i$ of the second sample 104 at a second aspecular angle 208.

The computer 112 may receive these values by manual entry by a user. For example, the user may receive these values from the display 214 of the measurement device 110 and input them into the computer 112 using the input device 114, e.g., the keyboard. However, in other embodiments (not shown), these values and/or other data may be transferred automatically between the measurement device 110 and the computer 112, e.g., via a USB port. Other techniques for transferring data between the measurement device 110 and the computer 112 may be realized by those skilled in the art. Furthermore, predicted data using color and sparkle predictive models may be transferred to the computer 112.

Figure 4:
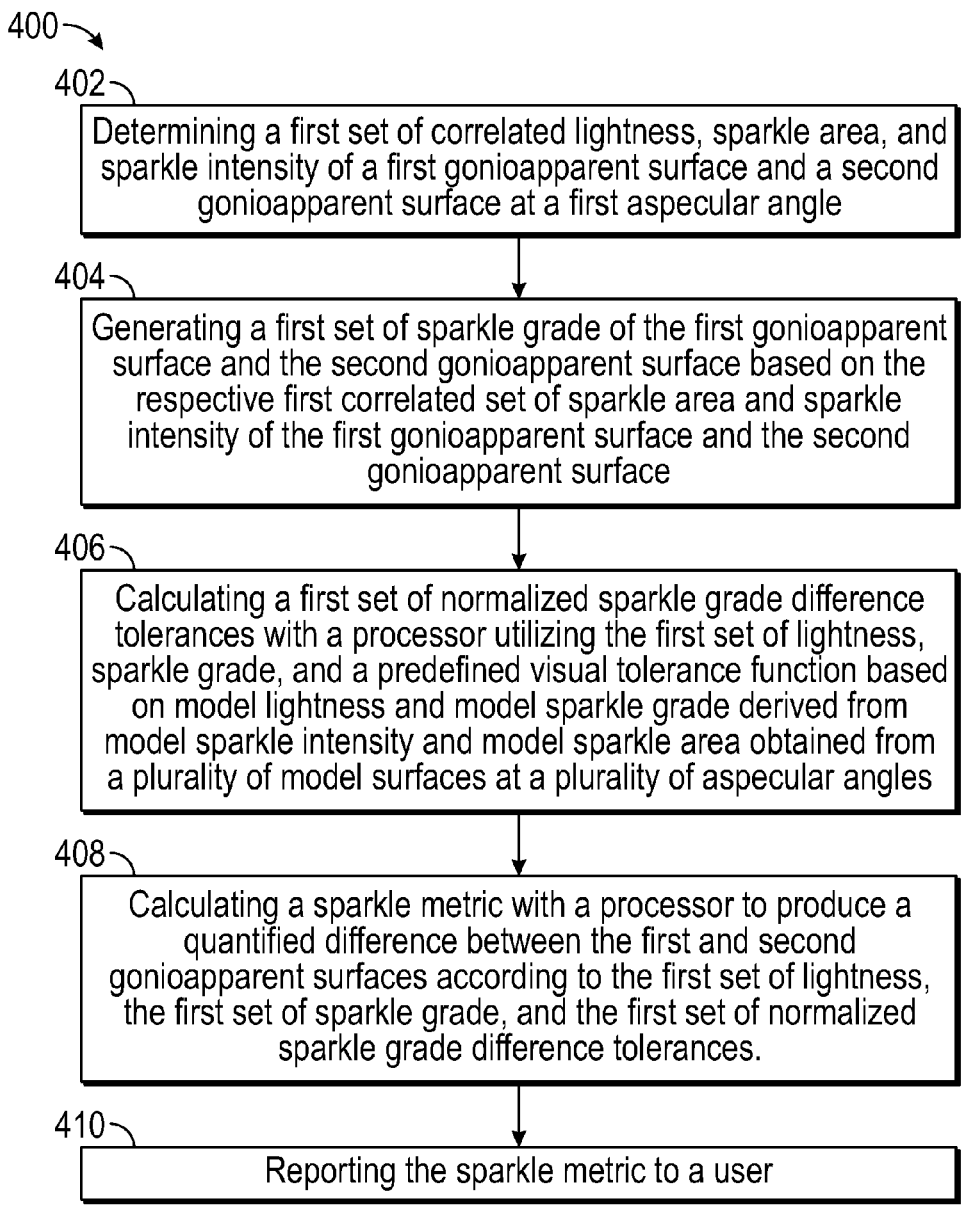
FIG. 4 shows a flowchart related to a method for comparing colored surfaces according to one embodiment.

As stated previously, and as illustrated in FIG. 4, the method 400 for quantifying differences between gonioapparent colored surfaces 102, 104 may utilize the system 100 described above and/or other suitable hardware. The method 400 includes, at 402, determining a first set of correlated lightness L*, sparkle area $S_a$, and sparkle intensity $S_i$ of the first gonioapparent surface 102 and the second gonioapparent surface 104 at a first aspecular angle 204. The method 400 may also include (not shown) determining a second set of lightness L*, sparkle area $S_a$, and sparkle intensity $S_i$ of the first gonioapparent surface 102 and the second gonioapparent surface 104 at the second aspecular angle 208.

The method 400 also includes, at 404, generating a first set of sparkle grade $S_g$ of the first gonioapparent surface 102 and the second gonioapparent surface 104 based on the respective first correlated set of sparkle area $S_a$ and sparkle intensity $S_i$ of the first gonioapparent surface 102 and the second gonioapparent surface 104. The method 400 may also include (not shown) generating a second set of sparkle grade $S_g$ of the first gonioapparent surface 102 and the second gonioapparent surface 104 based on the respective second correlated set of sparkle area $S_a$ and sparkle intensity $S_i$ of the first gonioapparent surface 102 and the second gonioapparent surface 104. In one exemplary embodiment, determining the sparkle grade $S_g$ is performed by the measurement device 110. However, this computation may alternatively be performed by the computer 112 when the corresponding sparkle areas $S_a$ and sparkle intensities $S_i$ are input thereto.

Figure 5:
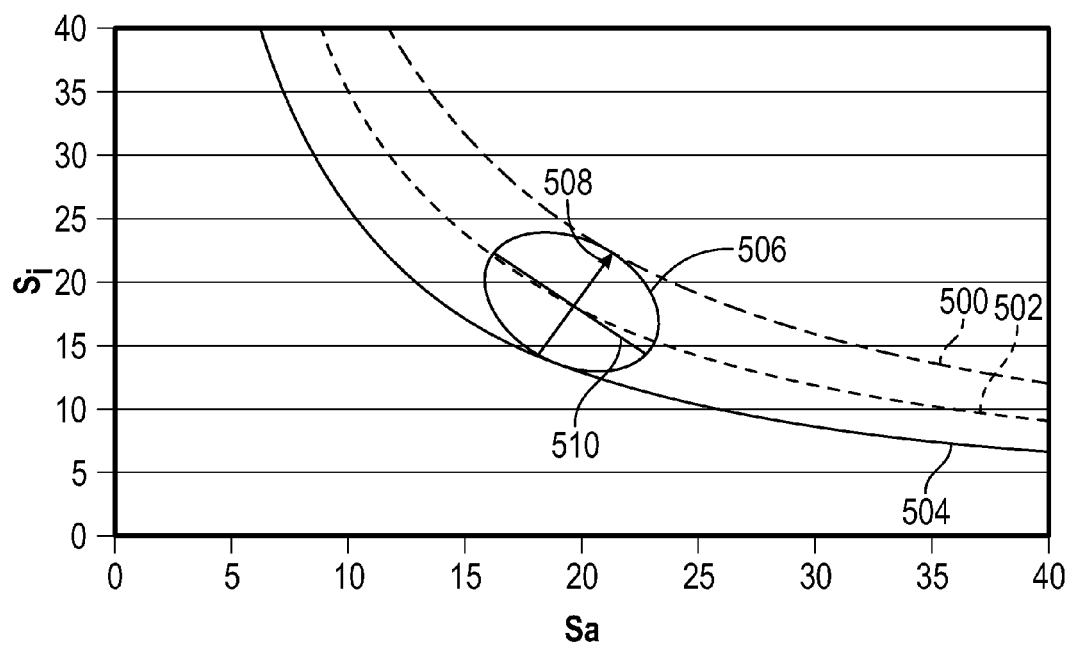
FIG. 5 is a graph showing different sparkle grades of three different surfaces and a tolerance ellipse for one of the surfaces according to one embodiment.

It should be appreciated that the sparkle grade $S_g$ value may not always correlate to visual perception of a surface 102, 104. For instance, FIG. 5 illustrates three different sparkle grades shown as three curves 500, 502, 504, where sparkle intensity $S_i$ is set on the vertical axis and sparkle area $S_a$ is set on the horizontal axis. As can be seen, very different values of sparkle area $S_a$ and sparkle intensity $S_i$ can be realized for a single sparkle grade $S_g$. Thus, utilizing sparkle grade $S_g$ alone to match surfaces 102, 104 can be problematic, as sparkle grade $S_g$ is not always correlated to visual perception of the surfaces 102, 104.

A tolerance ellipse 506, having a short axis 508 and a long axis 510, may be defined to correlate with the sparkle grade $S_g$ curve 502 of one of the surfaces 102, 104. The long axis 510 is tangent to the sparkle grade $S_g$ curve 502 at a point such that the tolerance ellipse 506 defines a region in which visually perceptible differences between the surfaces 102, 104 is not normally evident.

In visual experiments and data analyses on sparkle measurements versus sparkle visual perception showed that the tolerance ellipse 506 is not uniform in sparkle perception. It has been discovered that the lightness (L*) and sparkle grade ($S_g$) modify the tolerance ellipse 506. In order to define the functional dependence of the tolerance ellipse 506 to these variables, experimental panel pair model surfaces were grouped into three partitions for lightness L* and three partitions for sparkle grade $S_g$ making a total of nine regions, e.g., a 3×3 grid (not shown). Visual experiments were then conducted on a set of over one hundred panel pairs and assessments by observers were made. Of course, numerous variations in the above described experiments can be made including, but not limited to, the number of partitions and the number of panel pairs.

As such, the size of the tolerance ellipse 506 is not constant for every sparkle grade $S_g$ value. That is, the size of the tolerance ellipse 506 may vary based on several factors including lightness L*. A sparkle grade difference tolerance $K_{sg}$ may be computed based on the sparkle grade $S_g$ and the lightness L*. Particularly, in the exemplary embodiment, the sparkle grade difference tolerance $K_{sg}$ is computed with the following equation:

$$K_{sg} = a_0 + a_1 \cdot S_g + a_2 \cdot L^* + a_3 \cdot S_g^2 + a_4 \cdot L^{*2} + a_5 \cdot L^* S_g$$

The factors $a_0$-$a_5$ are found by a regression analysis. Specifically, these factors are $a_0 = 1.035$, $a_1 = -1.3$, $a_2 = -0.674$, $a_3 = 0.741$, $a_4 = 0.271$, and $a_5 = 1.24$. These factors are derived from the data located within a predefined partition using the model surfaces described above. The actual lightness value L* and sparkle grade values $S_g$ from the testing surfaces may be used to calculate the sparkle grade difference tolerance $K_{sg}$ at that particular angle.

The method 400 also includes, at 406, calculating a first set of normalized sparkle grade difference tolerances $K_{sg}$ with a processor utilizing the first set of lightness L*, sparkle grade $S_g$, and a predefined visual tolerance function $K_{sg}$ based on model lightness L* and model sparkle grade $S_g$ derived from a model sparkle intensity $S_i$ and model sparkle area $S_a$ obtained from a plurality of model surfaces at a plurality of aspecular angles 204, 208. The method 400 may also include (not shown) calculating a second set of normalized sparkle grade difference tolerances $K_{sg}$ with a processor utilizing the second set of lightness L*, sparkle grade $S_g$, and the predefined visual tolerance function $K_{sg}$ based on model lightness L* and model sparkle grade $S_g$ derived from a model sparkle intensity $S_i$ and model sparkle area $S_a$ obtained from a plurality of model surfaces at the plurality of aspecular angles 204, 208. Further, additional sets of normalized sparkle grade difference tolerances $K_{sg}$ may be calculated at other aspecular angles, e.g., 300.

The predefined visual tolerance function $K_{sg}$ may be determined by partitioning a plurality of model surfaces into n partitions based on the correlated model lightness L*, the model sparkle grade ($S_g$) at the plurality of aspecular angles 204, 208, 302 wherein n is an integer in a range from 2 to 100. The sparkle difference of the plurality of model surfaces at the respective aspecular angles 204, 208, 302 is then visually assessed. Individual visual tolerance functions $K_{sg}$ for each of the n partitions are then generated so a calculated sparkle difference between a pair of the model surfaces has the best fit with the visually assessed sparkle difference. In one embodiment, the model surfaces may be partitioned based on chroma and/or coarseness. In summary, the predefined visual tolerance functions for each partition, e.g., $K_{sg}^1$, $K_{sg}^2$, etc., may be calculated utilizing the equation:

$$K_{sg}^n = f^n(L^*, S_g)$$

The method 400 further includes, at 408, calculating a sparkle metric SpkM with a processor to produce a quantified difference between the first and second gonioapparent surfaces according to the first correlated set of lightness L*, the first set of sparkle grade $S_g$, and the first set of normalized sparkle grade difference tolerances. In another embodiment, the sparkle metric may be calculated with a processor to produce a quantified difference between the first and second gonioapparent surfaces according to the first and second sets of lightness L*, the first and second sets of sparkle grade $S_g$, and the first and second sets of normalized sparkle grade difference tolerances.

The sparkle metric SpkM quantifies the difference in appearance between the first and second surfaces 102, 104. That is, the sparkle metric SpkM is a number that tells how well matched the second surface 104 is from the first surface 102. The sparkle metric SpkM is a positive, real number between zero and infinity. A perfect match in surfaces would have a sparkle metric SpkM of zero. Generally, the higher the sparkle metric SpkM, the greater the difference in appearance between the surfaces 102, 104.

The method 400 may also include, at 410, reporting the sparkle metric SpkM to a user for analysis. In one embodiment, the sparkle metric SpkM may be reported to the user on the output device 116 of the computer 112. Other techniques to report the sparkle metric SpkM to the user are well known to those skilled in the art.

The sparkle metric SpkM may be integrated with color metrics and other appearance metrics to have an integrated color and appearance metric. These metrics may include, but are not limited to, color data, color difference data, appearance data, and appearance difference data. Such data and metrics, along with methods and techniques to obtain such data and metrics are disclosed in PCT International Publication No. WO 2013/049792, which is hereby incorporated by reference. Particularly, appearance difference data may include coarseness, texture, and/or sparkle size. As such, calculating the sparkle metric SpkM may include utilizing at least one of the color data, the color difference data, the appearance data, and the appearance difference data.

The method 400 may also include (not shown) calculating an ellipse angle φ of the tolerance ellipse 506 for the first surface 102 at the first aspecular angle 204 and the second aspecular angle 208 utilizing the corresponding sparkle areas Sa and sparkle intensities Si. Specifically, in the exemplary embodiment, the ellipse angle φ is computed with the following equation:

$$\varphi = \arctan\left(-\frac{S_i}{S_a}\right)$$

The method 400 may further include (not shown) calculating a short axis 508 length st of the tolerance ellipse 506 for the first surface 102 at the first aspecular angle 204 and the second aspecular angle 208 utilizing the corresponding ellipse angles φ and sparkle grade difference tolerances $K_{sg}$. Specifically, in the exemplary embodiment, the short axis 508 length st is computed with the following equation:

$$st = C \cdot K_{sg} \cdot \frac{1}{\cos(\varphi)}$$

wherein C is a constant. The constant C is determined by visual experiments to produce the best correlation of measurements to visual assessments.

The method 400 may further include (not shown) calculating a long axis 510 length lg of the tolerance ellipse 506 for the first sample 102 at the first aspecular angle 204 and the second aspecular angle 208 utilizing the short axis 508 length st. Specifically, in the exemplary embodiment, the long axis 510 length lg is computed with the following equation:

$$lg = ls\_ratio \cdot st$$

wherein ls_ratio is a constant. More specifically, ls_ratio is determined by visual experiments to produce the best correlation of measurements to visual assessments.

The method 400 may also include (not shown) calculating a first sparkle difference $\Delta S_1$ between the first sample 102 and the second sample 104 at the first aspecular angle 204 and calculating a second sparkle difference $\Delta S_2$ between the first sample 102 and the second sample 104 at the second aspecular angle 208 Specifically, the sparkle differences $\Delta S_1$, $\Delta S_2$ are determined utilizing the corresponding sparkle areas $S_a$ and sparkle intensities Si of the first and second samples 102, 104 at the first and second aspecular angles 204, 208 and the corresponding ellipse angles $\varphi$, short axis 508 lengths st, and long axis 510 lengths lg of the first sample 102 at the first and second aspecular angles 204, 208.

More specifically, in the exemplary embodiment, each sparkle difference is calculating using the following equation:

$$\Delta S = \sqrt{\left(\frac{dS_a \cdot \cos(\varphi) + dS_i \cdot \sin(\varphi)}{lg}\right)^2 + \left(\frac{-dS_a \cdot \sin(\varphi) + dS_i \cdot \cos(\varphi)}{st}\right)^2}$$

wherein $dS_a$ is the difference between the sparkle areas $S_a$ of the first and second surfaces 102, 104 and $dS_i$ is the difference between the sparkle intensities $S_i$ of the first and second surfaces 102, 104, at each respective aspecular angle 204, 208. Of course, in other embodiments, other sparkle differences may be calculated due to additional measurements at other aspecular angles.

In yet another embodiment, the sparkle metric SpkM may be calculated utilizing the first sparkle difference $\Delta S_1$ and the second sparkle difference $\Delta S_2$. More specifically, in this particular embodiment, the sparkle metric SpkM is calculating using the following equation:

$$SpkM = w_1 \cdot \Delta S_1 + w_2 \cdot \Delta S_2$$

wherein $w_1$ is a weight of 0.4 and $w_2$ is a weight of 0.4. The weights of 0.4 serve to reduce the number of false positive matches between samples.

In other embodiments, where more than two aspecular angle measurements are utilized, the sparkle metric SpkM may be calculated using the following equation:

$$SpkM = \sum_{j=1}^{n} w_j \Delta S_j$$

wherein $w_j$ is a weight corresponding to each angle that may be obtained by a visual assessment. It should be noted that sparkle metric SpkM is a function of $\Delta Sj$. As such, sparkle metric SpkM may be any function that produces a better correlation with a visual assessment.

The present invention has been described herein in an illustrative manner, and it is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

What is claimed is:

1. A method of quantifying a difference between a first gonioapparent surface and a second gonioapparent surface, said method comprising:
    illuminating the first gonioapparent surface at a first aspecular angle and at a second aspecular angle different from the first angle and the second gonioapparent surface at the first aspecular angle and at the second aspecular angle using a light source;
    sensing light reflected off the first and second surfaces at the respective first and second aspecular angles using a sensor;
    determining a first set of correlated lightness (L*), sparkle area ($S_a$), and sparkle intensity ($S_i$) of the first gonioapparent surface and the second gonioapparent surface at the first aspecular angle using a processor in communication with said sensor;
    generating a first set of sparkle grade ($S_g$) of the first gonioapparent surface and the second gonioapparent surface based on the respective first correlated set of sparkle area ($S_a$) and sparkle intensity ($S_i$) of the first gonioapparent surface and the second gonioapparent surface using a computer processor of a computer configured to receive the sparkle area ($S_a$) and the sparkle intensity ($S_i$) of the first and second gonioapparent surfaces at the first and second aspecular angles;
    calculating a first set of normalized sparkle grade difference tolerances ($K_{sg}$) utilizing the first set of lightness (L*), sparkle grade ($S_g$), and a predefined visual tolerance function ($K_{sg}$) based on model lightness (L*) and model sparkle grade ($S_g$) derived from model sparkle intensity ($S_i$) and model sparkle area ($S_a$) obtained from a plurality of model surfaces at a plurality of aspecular angles using the computer processor of the computer, which is further configured to receive the lightness (L*) of the first and second surfaces at the first and second aspecular angles; and
    calculating a sparkle metric (SpkM) to produce a quantified difference between the first and second gonioapparent surfaces according to the first set of lightness (L*), the first set of sparkle grade ($S_g$), and the first set of normalized sparkle grade difference tolerances ($K_{sg}$) using the computer processor of the computer.

2. The method as set forth in claim 1 wherein the predefined visual tolerance function ($K_{sg}$) is calculated with the computer processor of the computer utilizing the equation $$K_{sg}{}^n = f^n(L^*, S_g),$$

wherein L* represents the model lightness, $S_g$ represents the model sparkle grade.

3. The method as set forth in claim 2 wherein the predefined visual tolerance function ($K_{sg}$) is determined by:
    partitioning a plurality of model surfaces with the computer processor of the computer into n partitions based on the correlated model lightness (L*) and the model sparkle grade ($S_g$), wherein n is an integer in a range from 2 to 100;
    visually assessing the sparkle difference of the plurality of model surfaces at the plurality of aspecular angles; and
    generating an individual visual tolerance function $K_{sg}$ with the computer processor of the computer for each of the n partitions so a calculated sparkle difference between a pair of the model surfaces has the best fit with the visually assessed sparkle difference.

4. The method as set forth in claim 3, wherein the plurality of model surfaces are also partitioned with the computer processor of the computer based on at least one of chroma or coarseness.

5. The method as set forth in claim 3, further comprising:
determining a second correlated set of lightness (L*), sparkle area ($S_a$), and sparkle intensity ($S_i$) of the first gonioapparent surface and the second gonioapparent surface at a second aspecular angle using the computer processor of the computer;
generating a second set of sparkle grade ($S_g$) of the first surface and the second surface based on the second correlated set of sparkle area ($S_a$) and sparkle intensity ($S_i$) of the first gonioapparent surface and the second gonioapparent surface using the computer processor of the computer; and
calculating a second set of normalized sparkle grade difference tolerances ($K_{sg}$) utilizing the second set of lightness (L*), sparkle grade ($S_g$), and the predefined visual tolerance function ($K_{sg}$) based on model lightness (L*) and model sparkle grade ($S_g$) derived from model sparkle intensity ($S_i$) and model sparkle area ($S_a$) obtained from a plurality of model surfaces at the plurality of aspecular angles using the computer processor of the computer;
wherein calculating the sparkle metric (SpkM) comprises calculating the sparkle metric (SpkM) with the computer processor of the computer to produce a quantified difference between the first and second gonioapparent surfaces according to the first and second sets of lightness (L*), the first and second sets of sparkle grade ($S_g$), and the normalized sparkle grade difference tolerances ($K_{sg}$).

6. The method as set forth in claim 1 further comprising:
obtaining at least one of color data, color difference data, appearance data, and appearance difference of the first and second surfaces;
wherein calculating the sparkle metric (SpkM) using the computer processor of the computer comprises utilizing at least one of the color data, the color difference data, the appearance data, and the appearance difference data.

7. The method as set forth in claim 6 wherein the appearance difference data includes at least one of coarseness, texture, and sparkle size.

8. The method as set forth in claim 1 further comprising reporting the sparkle metric (SpkM) to a user using the computer processor of the computer.

9. The method as set forth in claim 1 further comprising calculating an ellipse angle ($\varphi$) of a tolerance ellipse with the computer processor of the computer for the first surface at the first aspecular angle and the second aspecular angle utilizing the corresponding sparkle areas ($S_a$) and sparkle intensities ($S_i$).

10. The method as set forth in claim 9 wherein calculating the ellipse angle ($\varphi$) comprises calculating the ellipse angle ($\varphi$) with the computer processor of the computer utilizing the equation $$\varphi = \arctan\left(-\frac{S_i}{S_a}\right).$$

11. The method as set forth in claim 3 further comprising determining a sparkle grade ($S_g$) of the first surface at the first and second aspecular angles with the computer processor of the computer utilizing the corresponding sparkle areas ($S_a$) and sparkle intensities ($S_i$).

12. The method as set forth in claim 11 further comprising calculating a short axis length (st) of the tolerance ellipse with the computer processor of the computer for the first surface at the first aspecular angle and the second aspecular angle utilizing the corresponding ellipse angles ($\varphi$) and sparkle grade difference tolerances ($K_{sg}$).

13. The method as set forth in claim 12 wherein calculating a short axis length (st) with the computer processor of the computer comprises calculating the short axis length (st) with the computer processor of the computer utilizing the equation $$st = C \cdot K_{sg} \cdot \frac{1}{\cos(\varphi)},$$

wherein C is a constant.

14. The method as set forth in claim 12 further comprising calculating a long axis length (lg) of the tolerance ellipse with the computer processor of the computer for the first surface at the first aspecular angle and the second aspecular angle utilizing the short axis length (st).

15. The method as set forth in claim 14 further comprising calculating a first sparkle difference ($\Delta S_1$) between the first surface and the second surface at the first aspecular angle with the computer processor of the computer utilizing the sparkle areas ($S_a$) and sparkle intensities ($S_i$) of the first and second surfaces at the first aspecular angle and the ellipse angle ($\varphi$), short axis length (st), and long axis length (lg) at the first aspecular angle.

16. The method as set forth in claim 15, wherein calculating the first sparkle difference ($\Delta S_1$) comprises calculating the first sparkle difference ($\Delta S_1$) with the computer processor of the computer utilizing the equation $$\Delta S_1 = \sqrt{\left(\frac{dS_a \cdot \cos(\varphi) + dS_i \cdot \sin(\varphi)}{lg}\right)^2 + \left(\frac{-dS_a \cdot \sin(\varphi) + dS_i \cdot \cos(\varphi)}{st}\right)^2},$$

wherein $dS_a$ is the difference between the sparkle areas ($S_a$) of the first and second surfaces at the first aspecular angle and $dS_i$ is the difference between the sparkle intensities ($S_a$) of the first and second surfaces at the first aspecular angle.

17. The method as set forth in claim 15 further comprising calculating a second sparkle difference ($\Delta S_2$) between the first surface and the second surface at the second aspecular angle with the computer processor of the computer utilizing the sparkle grades ($S_g$) and sparkle intensities ($S_i$) of the first and second surfaces at the second aspecular angle and the ellipse angle ($\varphi$), short axis length (st), and long axis length (lg) at the second aspecular angle.

18. The method as set forth in claim 17, wherein calculating the second sparkle difference ($\Delta S_2$) comprises calculating the second sparkle difference ($\Delta S_2$) with the computer processor of the computer utilizing the equation $$\Delta S_2 = \sqrt{\left(\frac{dS_a \cdot \cos(\varphi) + dS_i \cdot \sin(\varphi)}{lg}\right)^2 + \left(\frac{-dS_a \cdot \sin(\varphi) + dS_i \cdot \cos(\varphi)}{st}\right)^2},$$

wherein $dS_a$ is the difference between the sparkle areas ($S_a$) of the first and second surfaces at the second aspecular angle and $dS_i$, is the difference between the sparkle intensities ($S_a$) of the first and second surfaces at the second aspecular angle.

19. The method as set forth in claim 17 wherein calculating the sparkle metric (SpkM) comprises calculating the sparkle metric (SpkM) with the computer processor of the computer utilizing the first sparkle difference ($\Delta S_1$) and the second sparkle difference ($\Delta S_2$).

20. The method as set forth in claim 1 wherein the first surface is a standard and wherein the second surface is included on an exterior paneling of automobile.

21. A system for quantifying a difference between a first gonioapparent colored surface and a second gonioapparent colored surface, said system comprising:

a measurement device including a light source for illuminating the first surface at a first aspecular angle and at a second aspecular angle different from the first angle and the second surface at the first aspecular angle and at the second aspecular angle, a sensor for sensing light reflected off the first and second surfaces at the respective first and second aspecular angles, and a processor in communication with said sensor for determining a lightness (L*), a sparkle area (Sa), and a sparkle intensity (Si) of the first and second surfaces at the respective first and second aspecular angles; and a computer comprising a computer processor configured to receive the lightness (L*), a sparkle area (Sa), and a sparkle intensity (Si) of the first and second surfaces at the first and second aspecular angles and calculate a sparkle metric (SpkM) to quantify the difference between the first and second surfaces utilizing the lightness (L*), the sparkle area (Sa), and the sparkle intensity (Si) of the first and second surfaces at the first and second aspecular angles.

* * * * *